(12) United States Patent
Caprotti et al.

(10) Patent No.: US 7,306,634 B2
(45) Date of Patent: Dec. 11, 2007

(54) IRON SALT DIESEL FUEL ADDITIVE COMPOSITIONS FOR IMPROVEMENT OF PARTICULATE TRAPS

(75) Inventors: Rinaldo Caprotti, Oxfordshire (GB); Robert J. Pilling, London (GB)

(73) Assignee: Infineum International Limited (GB)

( * ) Notice: Subject to any disclaimer, the term of this patent is extended or adjusted under 35 U.S.C. 154(b) by 274 days.

(21) Appl. No.: 10/440,996

(22) Filed: May 19, 2003

(65) Prior Publication Data
US 2004/0068921 A1   Apr. 15, 2004

(30) Foreign Application Priority Data
Jul. 3, 2002   (EP) .................. 02254664

(51) Int. Cl.
*C10L 1/18* (2006.01)
*C10L 1/24* (2006.01)
*C10L 1/26* (2006.01)
*C10L 1/30* (2006.01)

(52) U.S. Cl. ............................ 44/358; 44/361; 44/362; 44/363; 44/365; 44/366

(58) Field of Classification Search .................. 44/358, 44/361, 362, 363, 365, 366
See application file for complete search history.

(56) References Cited

U.S. PATENT DOCUMENTS

| 5,539,135 A | 7/1996 | Breuer et al. ................ 554/167 |
| 6,488,725 B1 * | 12/2002 | Vincent et al. ................ 44/358 |
| 6,881,235 B2 * | 4/2005 | May ........................... 44/363 |

FOREIGN PATENT DOCUMENTS

| EP | 0 188 116 A1 | 7/1986 |
| EP | 0 471 583 A1 | 2/1992 |
| EP | 1 310 545 A1 | 5/2003 |
| FR | 2172797 | 2/1972 |
| GB | 1600449 | 10/1981 |
| GB | 2248068 | * 3/1992 |
| WO | WO92/17405 A1 | 10/1992 |
| WO | WO02/10317 A1 | 2/2002 |

* cited by examiner

*Primary Examiner*—Cephia D. Toomer

(57) ABSTRACT

A fuel additive iron salt composition effective in improving the operation of diesel engine particulate traps when added to a diesel fuel so as to provide 1-25 ppm iron in the fuel which comprises an oil soluble or oil dispersible neutral or overbased iron salt of an acidic organic compound, 50-99 mole % of the total iron present in the composition being in the ferric form, the balance being the ferrous form.

16 Claims, No Drawings

IRON SALT DIESEL FUEL ADDITIVE COMPOSITIONS FOR IMPROVEMENT OF PARTICULATE TRAPS

This invention relates to novel fuel additive compositions. More particularly, this invention relates to an iron salt additive composition which has been found highly effective in improving the quality of emissions from the combustion of diesel fuels. These additives are especially effective in improving the performance of particulate traps which are used in the exhaust systems of diesel engines, amongst other uses.

Diesel engines equipped with particulate traps, mounted in the exhaust stream, to "trap" or collect particulates in the exhaust to prevent their emission to the atmosphere are expected to be in greater use in the next few years.

Diesel engines running without particulate traps emit unburned hydrocarbons (HC), carbon monoxide (CO), nitrogen oxides ($NO_x$), and particulates, all of which are subject to current or proposed regulation. The problems of controlling these pollutants are compounded because there is a trade-off between particulates and nitrogen oxides—when the combustion conditions are modified to favor low nitrogen oxides emissions, particulates are increased. Particulate traps are employed to reduce the severity of the particulate emissions.

It now appears that a combination of techniques, including diesel traps and systems that use nitrogen oxides, will be required to meet realistic clean air goals. This manner of reducing particulates will be necessary because the techniques available for $NO_x$ reduction, such as timing changes and exhaust gas recirculation, require a trade-off with particulates. The achievement of lower emissions of $NO_x$, unburned hydrocarbons, and carbon monoxide, while controlling particulates over reasonable periods of time, continues to present a technical challenge.

Diesel particulates, their effect and control, are at the center of much concern and controversy. Their chemistry and environmental impact present complex issues. Generally, the diesel particulate matter is principally solid particles of carbon and metal compounds with adsorbed hydrocarbons, sulfates and aqueous species. Among the adsorbed species are aldehydes and polycyclic aromatic hydrocarbons. Some of these organics have been reported to be potential carcinogens or mutagens. Unburned hydrocarbons are related to the characteristic diesel odor and include aldehydes such as formaldehyde and acrolein. The need to control nano-particles is likely to lead to mandates requiring traps.

Unfortunately, increasing the recovery of particulates simply by modifying trap design or size would increase the rate of back pressure buildup within the trap, which causes increased fuel consumption and poor driveability. Moreover, control of the various pollutants seems to be interrelated, with reduction of one sometimes increasing levels of another. By modifying combustion to achieve more complete oxidation, decreases can be achieved for pollutants resulting from incomplete combustion, but $NO_x$ is typically increased under these conditions.

It is clear that diesel traps (either catalyzed or uncatalyzed) will be required in order to control particulates, especially where efforts are made to control $NO_x$.

The use of diesel traps and the need to improve them has resulted in a great deal of research and a great number of patents and technical publications. The traps are typically constructed of metal or ceramic and are capable of collecting the particulates from the exhaust and withstanding the heat produced by oxidation of carbonaceous deposits which must be burned off at regular intervals.

This burning off, or regeneration, could occur by itself if the operating temperature of the trap were sufficiently high. However, in the typical situation, the exhaust temperature is not constantly high enough, and secondary measures such as electrically heating to raise the trap temperature or using a catalyst on the washcoat to reduce the combustion temperature of particulates, have not been fully successful.

The use of organometallic salts and complexes to improve the operation of diesel engine particulate traps is disclosed, for example, in U.S. Pat. No. 5,344,467 issued Sep. 6, 1994, which teaches the use of a combination of an organometallic complex and an antioxidant. The organometallic complex is soluble or dispersible in the diesel fuel and is derived from an organic compound containing at least two functional groups attached to a hydrocarbon linkage.

WO099/36488 published Jul. 22, 1999 discloses fuel additive compositions which contain at least one iron-containing fuel-soluble or fuel-dispersible species in synergistic combination with at least one alkaline earth group metal-containing fuel-soluble or fuel-dispersible species. This combination of metallic additives is said to improve the operation of the diesel particulate filter traps.

Also pertinent to the subject matter of this invention is U.S. Pat. No. 4,946,609 issued Aug. 7, 1990, which teaches the use of iron compounds such as ferrocene, ferrocene derivatives and iron salts of organic acids as additives for lubricating oils used for diesel engines. It is taught that the presence of the iron compounds in the lubricating oil facilitates the regeneration of the diesel particle filters.

WO094/11467 published May 26, 1994 teaches a method to improve the operation of diesel traps through the use of a fuel additive comprising fuel-soluble compositions of a platinum group metal in effective amounts to lower the emissions of unburned hydrocarbons and carbon monoxide from the trap. The platinum group metals comprise platinum, palladium, rhodium or iridium.

The present invention is based upon the discovery that a certain neutral or overbased iron salt additive composition with certain relative amounts of ferric (Fe+3) and ferrous (Fe+2) components is a stable additive system and is effective in fuel in improving the operation of diesel engine particulate traps.

In accordance with the present invention, there has been discovered a fuel additive iron salt composition effective in improving the operation of diesel engine particulate traps when added to a diesel fuel so as to provide 1-25 ppm, such as 2-10 ppm or 5-10 ppm by weight iron in the fuel, which comprises an oil soluble or oil dispersible neutral or overbased iron salt of an acidic organic compound, 50-99 mole % of the total iron in the composition being in the ferric form, the balance being the ferrous form. The term "total iron" refers to the iron present in both the salt as well as the iron present in the iron compound used to provide the excess iron when an overbased salt composition is used.

Improved diesel fuel oils containing 1-25 ppm iron from the compositions of this invention constitute further embodiments of this invention. Suitable fuel oils are described below.

A further embodiment comprises the method of improving the operation of a diesel engine particulate trap by providing to the engine a diesel fuel composition containing additive compositions of this invention.

Stable solutions or dispersions of the additive compositions of this invention in a suitable solvent comprise a further embodiment of this invention. Such additive concentrates will contain 20 to 80% of active material. The active materials are present in the solvent in such amounts so as to provide in the fuel 1-25 ppm of iron.

The solvent used to prepare the stable additive solutions or dispersions may generally be characterized as a normally liquid petroleum or synthetic hydrocarbon or oxygenated hydrocarbon or alcohol solvents, such as hexanol, 2-ethylhexanol or isodecyl alcohol solvent. Typical examples include kerosene, hydrotreated kerosene, isoparaffinic and paraffinic solvents and naphthenic aliphatic hydrocarbon solvents, aromatic solvents, dimers and higher oligomers or propylene, butene and similar olefins and mixtures thereof. Commercial products such as "Solvesso", "Varsol", "Norpar" and "Isopar" are suitable. Such solvents may also contain functional groups other than carbon and hydrogen provided such groups do not adversely affect the performance of the additive composition. Preferred are isoparaffinic and paraffinic hydrocarbon solvents. Preferably, the solvent has a flash point greater than 20° C., more preferably greater than 40° C., most preferably greater than 55° C.

The iron salt compositions are composed of 50-99 mole %, based on the total iron present, of the ferric form of iron such as iron salt compositions composed of 60%, 70%, 80% or 90 mole % of the ferric form, the balance being the ferrous form. It has been found that such compositions rich in the ferric form of iron exhibit greater stability in hydrocarbon fluids over extended periods of time and wide temperature ranges as exhibited by a reduced tendency to cause the formation of sediment as compared with ferrous materials.

An overbased salt will contain a stoichiometric excess of iron species to salt anions. This excess metal may exist in one or a combination of forms including oxides, hydroxides or mixed oxidic salts. Lattice-like polynuclear-iron complexes may also be present. A neutral salt contains a stoichiometric ratio of iron species to anions. The amount of excess iron may be 5-85 wt. % of a stoichiometric excess over that required to neutralize the anionic portion of the salt, such as 5-85, 5-50, 5-25 or 20-50 wt. %.

When the fuel additive of this invention is overbased, it means that the excess iron may be introduced, either intentionally or unintentionally, during the main reaction process of salt formation or alternatively may be introduced subsequent to this via post treatment. The elemental iron, oxides and hydroxides are common feedstocks for the overbasing process.

In one embodiment of the invention the additive is admixed with the diesel fuel by direct addition, or as part of a concentrate with other additives, and the diesel fuel is used to operate a diesel engine equipped with an exhaust system particulate trap. The diesel fuel containing the additive is contained in a fuel tank, transmitted to the diesel engine where it is burned, and the additive reduces the ignition temperature of exhaust particles collected in the exhaust system particulate trap. In another embodiment, the foregoing operational procedure is used except that the additive combination is maintained on board the apparatus being powered by the diesel engine (e.g., automobile, bus, truck, etc.) in a separate fuel additive dispenser apart from the diesel fuel. The additive is combined or blended with the diesel fuel during re-filling of the diesel fuel tank. Typically, the additive is dispensed in the form of a solution in a hydrocarbon solvent. In this latter embodiment, the additive is maintained in the fuel additive dispenser and can form a part of a fuel additive concentrate of the concentrate being combined with the diesel. Other techniques comprise adding the additive combination into the intake or exhaust manifold or adding the additive to the fuel at fuel depots prior to filling the tank of the diesel powered vehicle.

The organic moiety of the iron salt compounds preferably contains at least one hydrocarbyl group, for example, as a substituent on an aromatic ring. The term "hydrocarbyl" as used herein means that the group concerned is primarily composed of hydrogen and carbon atoms and is bonded to the remainder of the molecule via a carbon atom but does not exclude the presence of other atoms or groups in a proportion insufficient to detract from the substantially hydrocarbon characteristics of the group. Advantageously, hydrocarbyl groups for use in accordance with the invention are aliphatic groups, preferably alkyl or alkylene groups, especially alkyl groups, which may be linear or branched. The total number of carbon atoms in the organic moiety should be at least sufficient to impart the desired oil-solubility or oil-dispersibility.

Phenols, for use in the iron salts of this invention, may be non-sulfurized or, preferably, sulfurized. Further, the term "phenol" as used herein includes phenols containing more than one hydroxyl group (for example, alkyl catechols) or fused aromatic rings (for example, alkyl naphthols) and phenols which have been modified by chemical reaction, for example, alkylene-bridged phenols and Mannich base-condensed phenols; and saligenin-type phenols (produced by the reaction of a phenol and an aldehyde under basic conditions).

Preferred phenols may be derived from the formula

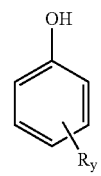

where R represents a hydrocarbyl group and y represents 1 to 4. Where y is greater than 1, the hydrocarbyl groups may be the same or different.

The phenols are frequently used in sulfurized form. Sulfurized hydrocarbyl phenols may typically be represented by the formula:

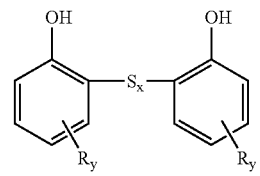

where x is generally from 1 to 4. In some cases, more than two phenol molecules may be linked by $S_x$ bridges.

In the above formulae, hydrocarbyl groups represented by R are advantageously alkyl groups, which advantageously contain 5 to 100, preferably 5 to 40, especially 9 to 12, carbon atoms, the average number of carbon atoms in all of the R groups being at least 9 in order to ensure adequate solubility in oil. Preferred alkyl groups are nonyl (tripropylene) groups.

In the following discussion, hydrocarbyl-substituted phenols will for convenience be referred to as alkyl phenols.

A sulfurizing agent for use in preparing a sulfurized phenol or phenate may be any compound or element which introduces —$(S)_x$— bridging groups between the alkyl phenol monomer groups, wherein x is generally from 1 to about 4. Thus, the reaction may be conducted with elemental sulfur or a halide thereof, for example, sulfur dichloride or, more preferably, sulfur monochloride. If elemental sulfur is used, the sulfurization reaction may be effected by heating the alkyl phenol compound at from 50 to 250, preferably at least 100, ° C. The use of elemental sulfur will typically yield a mixture of bridging groups —$(S)x$— as described above. If a sulfur halide is used, the sulfurization reaction may be effected by treating the alkyl phenol at from −10 to 120, preferably at least 60, ° C. The reaction may be conducted in the presence of a suitable diluent. The diluent advantageously comprises a substantially inert organic diluent, for example mineral oil or an alkane. In any event, the reaction is conducted for a period of time sufficient to effect substantial reaction. It is generally preferred to employ from 0.1 to 5 moles of the alkyl phenol material per equivalent of sulphurizing agent.

Where elemental sulfur is used as the sulfurizing agent, it may be desirable to use a basic catalyst, for example, sodium hydroxide or an organic amine, preferably a heterocyclic amine (e.g., morpholine).

Details of sulfurization processes are well known to those skilled in the art.

Regardless of the manner in which they are prepared, sulfurized alkyl phenols useful in preparing overbased metal compounds generally comprise diluent and unreacted alkyl phenols and generally contain from 2 to 20, preferably 4 to 14, and most preferably 6 to 12, mass % sulfur based on the mass of the sulfurized alkyl phenol.

As indicated above, the term "phenol" as used herein includes phenols that have been modified by chemical reaction with, for example, an aldehyde, and Mannich base-condensed phenols.

Aldehydes with which phenols may be modified include, for example, formaldehyde, propionaldehyde and butyraldehyde. The preferred aldehyde is formaldehyde Aldehyde-modified phenols suitable for use are described in, for example, U.S. Pat. No. 5,259,967.

Mannich base-condensed phenols are prepared by the reaction of a phenol, an aldehyde and an amine. Examples of suitable Mannich base-condensed phenols are described in GB-A-2 121 432.

In general, the phenols may include substituents other than those mentioned above provided that such substituents do not detract significantly from the surfactant properties of the phenols. Examples of such substituents are methoxy groups and halogen atoms.

Salicylic acids used for salicylate salts of the invention may be non-sulfurized or sulfurized, and may be chemically modified and/or contain additional substituents, for example, as discussed above for phenols. Processes similar to those described above may also be used for sulfurizing a hydrocarbyl-substituted salicylic acid, and are well known to those skilled in the art. Salicylic acids are typically prepared by the carboxylation, by the Kolbe-Schmitt process, of phenoxides, and in that case, will generally be obtained (normally in a diluent) in admixture with uncarboxylated phenol.

Preferred substituents in oil-soluble salicylic acids from which overbased detergents in accordance with the invention may be derived are the substituents represented by R in the above discussion of phenols. In alkyl-substituted salicylic acids, the alkyl groups advantageously contain 5 to 100, preferably 9 to 30, especially 14 to 20, carbon atoms.

Sulfonic acids used for iron sulfonate salts of this invention are typically obtained by sulfonation of hydrocarbyl-substituted, especially alkyl-substituted, aromatic hydrocarbons, for example, those obtained from the fractionation of petroleum by distillation and/or extraction, or by the alkylation of aromatic hydrocarbons. Examples include those obtained by alkylating benzene, toluene, xylene naphthalene, biphenyl or their halogen derivatives, for example, chlorobenzene, chlorotoluene or chloronaphthalene. Alkylation of aromatic hydrocarbons may be carried out in the presence of a catalyst with alkylating agents having from 3 to more than 100 carbon atoms, such as, for example, haloparaffins, olefins that may be obtained by dehydrogenation of paraffins, and polyolefins, for example, polymers of ethylene, propylene, and/or butene. The alkylaryl sulphonic acids usually contain from 7 to 100 or more carbon atoms. They preferably contain from 16 to 80, or 12 to 40, carbon atoms per alkyl-substituted aromatic moiety, depending on the source from which they are obtained.

When neutralizing these alkylaryl sulfonic acids to provide sulfonates, hydrocarbon solvents and/or diluent oils may also be included in the reaction mixture, as well as promoters and viscosity control agents.

Another type of sulfonic acid that may be used in accordance with the invention comprises alkyl phenol sulfonic acids. Such sulfonic acids can be sulfurized. Whether sulfurized or non-sulfurized these sulfonic acids are believed to have surfactant properties comparable to those of sulfonic acids, rather than surfactant properties comparable to those of phenols.

Sulfonic acids suitable for use in accordance with the invention also include alkyl sulfonic acids, such as alkenyl sulfonic acids. In such compounds the alkyl group suitably contains 9 to 100, advantageously 12 to 80, especially 16 to 60, carbon atoms.

Carboxylic acids that may be used in accordance with the invention include mono- and dicarboxylic acids. Preferred monocarboxylic acids are those containing 1 to 30, especially 8 to 24, carbon atoms. (Where this specification indicates the number of carbon atoms in a carboxylic acid, the carbon atom(s) in the carboxylic group(s) is/are included in that number.) Examples of monocarboxylic acids are iso-octanoic acid, stearic acid, oleic acid, palmitic acid and behenic acid. Other examples are tall oil fatty acid, soy acid and acid derived from rapeseed oil. Iso-octanoic acid may, if desired, be used in the form of the mixture of $C_8$ acid isomers sold by ExxonMobil Chemical Co. under the trade name "Cekanoic". Other suitable acids are those with tertiary substitution at the α-carbon atom and dicarboxylic acids with more than 2 carbon atoms separating the carboxylic groups. Further, dicarboxylic acids with more than 35, for example, 36 to 100, carbon atoms are also suitable. Unsaturated carboxylic acids can be sulphurized. Although salicylic acids contain a carboxylic group, for the purposes of the present invention they are considered to be a separate group of surfactants, and are not considered to be carboxylic acid surfactants. (Nor, although they contain a hydroxyl group, are they considered to be phenol surfactants.)

Other acids are those formed by dimerizing fatty acids such as $C_{36}$ dimer acid and $C_{12}$-$C_{90}$, $C_{12}$-$C_{40}$ or $C_{12}$-$C_{24}$ succinic anhydride hydrolysis products or acids derived from polyalkenyl-maleic anhydride reaction products.

Preferred are metal salts of naphthenic acids which are monocarboxylic acids related to the naphthene series of hydrocarbons. The naphthenic acids are defined as monocarboxylic acids of the naphthene series of hydrocarbons. Their general formula may be written $R(CH_2)_n COOH$ where R is a cyclic moiety composed of one or more rings. These rings are usually 5-membered (cyclo-pentene) and may be alkylated.

Examples of other compounds that may be used to provide iron salt additives in accordance with the invention include the following compounds, and derivatives thereof: naphthenic acids, especially naphthenic acids containing one or more alkyl groups, dialkylphosphonic acids, dialkylthiophosphonic acids, and dialkyldithiophosphoric acids, high molecular weight (preferably ethoxylated) alcohols, dithiocarbamic acids, thiophosphines, and dispersants. Surfactants of these types are well known to those skilled in the art. Surfactants of the hydrocarbyl-substituted carboxylalkylene-linked phenol type, or dihydrocarbyl esters of alkylene dicarboxylic acids, the alkylene group being substituted with a hydroxy group and an additional carboxylic acid group, or alkylene-linked polyaromatic molecules, the aromatic moieties whereof comprise at least one hydrocarbyl-substituted phenol and at least one carboxy phenol, may also be suitable for use in the present invention; such surfactants are described in EP-A-708 171.

As used in this specification the term "hydrocarbyl" refers to a group having a carbon atom directly attached to the rest of the molecule and having a hydrocarbon or predominantly hydrocarbon character. Examples include hydrocarbon groups, including aliphatic (e.g. alkyl or alkenyl), alicyclic (e.g. cycloalkyl or cycloalkenyl), aromatic, and alicyclic-substituted aromatic, and aromatic-substituted aliphatic and alicyclic groups. Aliphatic groups are advantageously saturated. These groups may contain non-hydrocarbon substituents provided their presence does not alter the predominantly hydrocarbon character of the group. Examples include keto, halo, hydroxy, nitro, cyano, alkoxy and acyl. If the hydrocarbyl group is substituted, a single (mono) substituent is preferred.

Preferred are the neutral or overbased iron salts or complexes derived from an acid compound of the formula

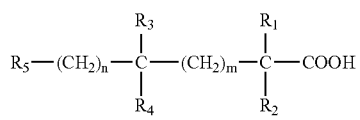

where $R_1$, $R_2$, $R_3$ and $R_4$ represent hydrogen or a hydrocarbyl having 1-30 carbon atoms ($C_1$-$C_{30}$), but at least two of $R_1$, $R_2$, $R_3$ or $R_4$ are $C_1$-$C_{30}$ hydrocarbyl; $R_5$ is a hydrocarbyl having 1 to 120 carbon atoms and m and n may each be zero or an integer such that the total number of carbon atoms in the carboxylate is not more than 125. The formula above is intended to represent a carboxylic acid which has at least two side chains of at least 1 to 30 carbon atoms in length, and preferably both $R_1$ and $R_2$ are hydrocarbyl so that the carboxylate is a neocarboxylate, i.e., having the carbon atom which is alpha to the carbonyl carbon connected to four other carbon atoms. The term hydrocarbyl is intended to apply to aromatic or aliphatic radicals composed principally of carbon and hydrogen, optionally substituted with oxygen or nitrogen, preferably aliphatic and particularly straight or branched chain alkyl or substituted alkyl, the substituents being nitrogen or oxygen. Most preferably the carboxylate is a neodecanoate.

Suitable examples of $R_5$ moieties are hydrocarbyl groups are made from homo- or interpolymers (e.g. copolymers, terpolymers) of mono- and di-olefins having 2 to 10 carbon atoms, such as ethylene, propylene, 1-butene, isobutene, butadiene, isoprene, 1-hexene, 1-octene, etc. Typically, these olefins are 1-monoolefins. This hydrocarbyl can also be derived from the halogenated (e.g. chlorinated or brominated) analogs of such homo- or interpolymers or from polyethers.

The hydrocarbyl is predominantly saturated. The hydrocarbyl is predominantly aliphatic in nature, that is, containing no more than one non-aliphatic moiety (cycloalkyl, cycloalkenyl or aromatic) group of 6 or less carbon atoms for every 10 carbon atoms in the substituent. Usually, however, the hydrocarbyl contains no more than one such non-aliphatic group for every 50 carbon atoms, and in many cases, they contain no such non-aliphatic groups at all; that is, the typical substituents are purely aliphatic. Typically, these purely aliphatic hydrocarbyls are alkyl or alkenyl groups.

A preferred source of the $R_5$ moiety are poly(isobutene)s obtained by polymerization of a $C_4$ refinery stream having a butene content of 35 to 75 wt. % and isobutene content of 30 to 60 wt. % in the presence of a Lewis acid catalyst such as aluminum trichloride or boron trifluoride. These polybutenes predominantly contain monomer repeating units of the configuration $-C(CH_3)_2CH_2-$.

Any fuel having a boiling range and viscosity suitable for use in a diesel-type compression ignition engine may be used in this invention.

Such fuel oils include "middle distillate" fuel oil which refers to petroleum-based fuel oils obtainable in refining crude oil as the fraction from the light, kerosene or jet fuel, fraction to the heavy fuel oil fraction. These fuel oils may also comprise atmospheric or vacuum distillate, cracked gas oil or a blend, in any proportions, of straight run and thermally and/or catalytically cracked distillate. Examples include kerosene, jet fuel, diesel fuel, heating oil, visbroken gas oil, light cycle oil, vacuum gas oil and hydrocracked streams. Such middle distillate fuel oils usually boil over a temperature range, generally within the range of 100° C. to 500° C., as measured according to ASTM D86, more especially between 150° C. and 400° C. Preferably, the diesel fuel will have less than 0.1% by weight sulfur, more preferably less than 0.05%, 0.005%, or 0.001% by weight sulfur as determined by ASTM D 2622-87.

Preferred vegetable-based fuel oils are triglycerides of monocarboxylic acids, for example, acids containing 10-25 carbon atoms, and typically have the general formula shown below

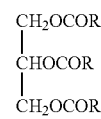

where R is an aliphatic radical of 10-25 carbon atoms which may be saturated or unsaturated.

Generally, such oils contain glycerides of a number of acids, the number and kind varying with the source vegetable of the oil.

Suitable fuel oils also include mixtures of 1-50%, 1-25% or 1-5% by weight of vegetable oils or methylesters of fatty acid, such as tall oil fatty acids, with petroleum based diesel fuel oils. Also suitable are fuels emulsified with water and alcohols, which contain suitable surfactants, and residual fuel oil used in marine diesel engines.

Examples of oils are tall oil, rapeseed oil, coriander oil, soyabean oil, soya oil, corn oil, cottonseed oil, sunflower oil, castor oil, olive oil, peanut oil, maize oil, almond oil, palm kernel oil, coconut oil, mustard seed oil, beef tallow and fish oils. Rapeseed oil, which is a mixture of fatty acids partially esterified with glycerol, is preferred as it is available in large quantities and can be obtained in a simple way by pressing from rapeseed.

Further preferred examples of vegetable-based fuel oils are alkyl esters, such as methyl esters, of fatty acids of the vegetable or animal oils. Such esters can be made by transesterification.

As lower alkyl esters of fatty acids, consideration may be given to the following, for example as commercial mixtures: the ethyl, propyl, butyl and especially methyl esters of fatty acids with 12 to 22 carbon atoms, for example of lauric acid, myristic acid, palmitic acid, palmitoleic acid, stearic acid, oleic acid, elaidic acid, petroselic acid, ricinoleic acid, elaeostearic acid, linoleic acid, linolenic acid, eicosanoic acid, gadoleic acid, docosanoic acid or erucic acid, which have an iodine number from 50 to 150, especially 90 to 125. Mixtures with particularly advantageous properties are those which contain mainly, i.e. to at least 50 wt % methyl esters of fatty acids with 16 to 22 carbon atoms and 1, 2 or 3 double bonds. The preferred lower alkyl esters of fatty acids are the methyl esters of oleic acid, linoleic acid, linolenic acid and erucic acid.

Commercial mixtures of the stated kind are obtained for example by cleavage and esterification of natural fats and oils by their transesterification with lower aliphatic alcohols. For production of lower alkyl esters of fatty acids it is advantageous to start from fats and oils with high iodine number, such as, for example, sunflower oil, rapeseed oil, coriander oil, castor oil, soyabean oil, cottonseed oil, peanut oil, corn oil, or beef tallow. Lower alkyl esters of fatty acids based on a new variety of rapeseed oil, the fatty acid component of which is derived to more than 80 wt % from unsaturated fatty acids with 18 carbon atoms, are preferred.

Most preferred as a vegetable-based fuel oil is rapeseed methyl ester.

The inventive diesel fuel compositions can contain other additives which are well known to those of skill in the art. These include dyes, cetane improvers, rust inhibitors such as alkylated succinic acids and anhydrides, bacteriostatic agents, gum inhibitors, metal deactivators, demulsifiers, upper cylinder lubricants, anti-icing agents, antioxidants and nitrogen containing ashless detergents such as polyalkylene amines and polyalkenyl succinimides.

The iron salt additive of this invention may also be used in combination with the various lubricity additives that are now commonly used in low sulfur fuels. Such lubricity additives include monohydric or polyhydric alcohol esters of $C_2$-$C_{50}$ carboxylic acids such as glycerol monooleate, esters of polybasic acids with $C_1$-$C_5$ monohydric alcohols, esters of dimerized carboxylic acids, reaction products of polycarboxylic acids and epoxides such as 1,2-epoxyethane and 1,2-epoxypropane and lubricity additives derived from fatty acids such as vegetable oil fatty acid methyl esters.

Further examples are lubricity additives prepared by combining the aforesaid esters of $C_2$-$C_{50}$ carboxylic acids with an ashless dispersant comprising an acylated nitrogen compound having a hydrocarbyl substituent of at least 10 carbon atoms made by reacting an acylating agent with an amino compound, such as the reaction products of polyisobutenyl ($C_{80}$-$C5_{00}$) succinic anhydride with ethylene polyamines having 3 to 7 amino nitrogen atoms.

Other lubricity additives are combinations of the aforesaid esters with ethylene-unsaturated ester copolymers having, in addition to units derived from ethylene, units of the formula

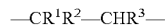

$$—CR^1R^2—CHR^3—$$

wherein $R^1$ represents hydrogen or methyl; $R^2$ represents $COOR^4$, wherein $R^4$ represents an alkyl group having from 1 to 9 carbon atoms which is straight chain or, if it contains 2 or more carbon atoms, branched, or $R^2$ represents $OOCR^5$, wherein $R^5$ represents $R^4$ or H; and $R^3$ represents H or $COOR^4$. Examples are ethylene-vinyl acetate and ethylene-vinyl propionate and other copolymers where there is present 5-40% of the vinyl ester.

As an alternative to the above described esters, or in combination therewith, the lubricity additive may comprise one or more carboxylic acids of the types disclosed in relation to the ester lubricity additives or vegetable based fuel oils. Such acids may be mono- or polycarboxylic, saturated or unsaturated, straight or branched chain and may be generalized by the formula $R^1(COOH)_x$ where x is 1-4 and $R^1$ is a $C_2$ to $C_{50}$ hydrocarbyl. Examples are capric, lauric, myristic, palmitic, oleic, elaidic, palmitoleic, petaoselic, ricinoleic, linoleic, linolemic, eicosanic, tall oil fatty and dehydrated castor oil fatty acids. The polycarboxylic acid may be a dimer acid such as that formed by dimerization of unsaturated fatty acids such as linoleic or oleic acid.

Other lubricity additives are hydroxy amines of the formula

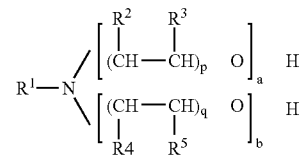

where R1 is an alkenyl radical having one or more double bonds or an alkyl radical and containing from 4 to 50 carbon atoms, or a radical of the formula

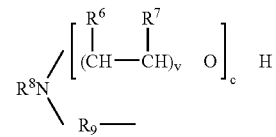

where each of $R^2$, $R^3$, $R^4$, $R^5$, $R^6$ and $R^7$ is independently hydrogen or a lower alkyl radical; $R^8$ is an alkenyl radical having one or more double bonds or an alkyl radical and containing from 4 to 50 carbon atoms; $R^9$ is an alkylene radical containing from 2 to 35, e.g. 2 to 6, carbon atoms; each of p, q and v is an integer between 1 and 4; and each of a, b and c may be O, providing that at least one of a, b or c is an integer between 1 and 75.

The additives of the invention may also be used in combination with diesel performance additives such as silicon-containing anti-foam agents such as siloxane block copolymers or cetane improvers such as 2-ethyl hexyl nitrate.

The additives of this invention may also be used in combination with cold flow additives such as an oil-soluble hydrogenated block diene polymer, comprising at least one crystallizable block, obtainable by end-to-end polymerization of a linear diene, and at least one non-crystallizable block, the non-crystallizable block being obtainable by 1,2-configuration polymerization of a linear diene, by polymerization of a branched diene, or by a mixture of such polymerizations, or another cold flow improver as defined in (A)-(F) below.

(A) An Ethylene-unsaturated Ester Copolymer, More Especially One Having, in Addition to Units Derived from Ethylene, Units of the Formula

wherein $R^3$ represents hydrogen or methyl, $R^4$ represents $COOR^6$, wherein $R^6$ represents an alkyl group having from 1 to 9 carbon atoms, which is straight chain or, if it contains 3 or more carbon atoms, branched, or $R^4$ represents $OOCR^7$, wherein $R^7$ represents $R^6$ or H, and $R^5$ represents H or $COOR^6$.

These may comprise a copolymer of ethylene with an ethylenically unsaturated ester, or derivatives thereof. An example is a copolymer of ethylene with an ester of a saturated alcohol and an unsaturated carboxylic acid, but preferably the ester is one of an unsaturated alcohol with a saturated carboxylic acid. An ethylene-vinyl ester copolymer is advantageous; an ethylene-vinyl acetate, ethylene-vinyl propionate, ethylene-vinyl hexanoate, or ethylene-vinyl octanoate copolymer is preferred.

As disclosed in U.S. Pat. No. 3,961,916, flow improver compositions may comprise a wax growth arrestor and a nucleating agent. Without wishing to be bound by any theory, the applicants believe that component (i) of the additive composition of the invention acts primarily as a nucleator and will benefit from the presence of an arrestor. This may, for example, be an ethylene-unsaturated ester as described above, especially an EVAC with a molecular weight (Mn, measured by gel permeation chromatography against a polystyrene standard) of at most 14000, advantageously at most 10000, preferably 2000 to 6000, and more preferably from 2000 to 5500, and an ester content of 7.5% to 35%, preferably from 10 to 20, and more preferably from 10 to 17, molar percent.

It is within the scope of the invention to include an additional nucleator, e.g., an ethylene-unsaturated ester, especially vinyl acetate, copolymer having a number average molecular weight in the range of 1200 to 20000, and a vinyl ester content of 0.3 to 10, advantageously 3.5 to 7.0 molar percent.

(B) A Comb Polymer

Such polymers are polymers in which branches containing hydrocarbyl groups are pendant from a polymer backbone, and are discussed in "Comb-Like Polymers. Structure and Properties", N. A. Platé and V. P. Shibaev, J. Poly. Sci. Macromolecular Revs., 8, p 117 to 253 (1974).

Generally, comb polymers have one or more long chain hydrocarbyl branches, e.g., oxyhydrocarbyl branches, normally having from 10 to 30 carbon atoms, pendant from a polymer backbone, said branches being bonded directly or indirectly to the backbone. Examples of indirect bonding include bonding via interposed atoms or groups, which bonding can include covalent and/or electrovalent bonding such as in a salt.

Advantageously, the comb polymer is a homopolymer having, or a copolymer at least 25 and preferably at least 40, more preferably at least 50, molar percent of the units of which have, side chains containing at least 6, and preferably at least 10, atoms.

As examples of preferred comb polymers there may be mentioned those of the general formula

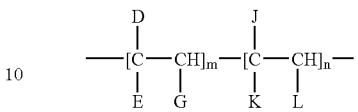

wherein
$D=R^{11}$, $COOR^{11}$, $OCOR^{11}$, $R^{12}COOR^{11}$, or $OR^{11}$,
$E=H$, $CH_3$, D, or $R^{12}$,
$G=H$ or D
$J=H$, $R^{12}$, $R^{12}COOR^{11}$, or an aryl or heterocyclic group,
$K=H$, $COOR^{12}$, $OCOR^{12}$, $OR^{12}$ or COOH,
$L=H$, $R^{12}$, $COOR^{12}$, $OCOR^{12}$, COOH, or aryl,
$R^{11} \geqq C_{10}$ hydrocarbyl,
$R^{12} \geqq C_1$ hydrocarbyl or hydrocarbylene, and m and n represent mole fractions, m being finite and preferably within the range of from 1.0 to 0.4, n being less than 1 and preferably in the range of from 0 to 0.6.

$R^{11}$ advantageously represents a hydrocarbyl group with from 10 to 30 carbon atoms, while $R^{12}$ advantageously represents a hydrocarbyl or hydrocarbylene group with from 1 to 30 carbon atoms.

The comb polymer may contain units derived from other monomers if desired or required.

These comb polymers may be copolymers of maleic anhydride or fumaric or itaconic acids and another ethylenically unsaturated monomer, e.g., an α-olefin, including styrene, or an unsaturated ester, for example, vinyl acetate or homopolymer of fumaric or itaconic acids. It is preferred but not essential that equimolar amounts of the comonomers be used although molar proportions in the range of 2 to 1 and 1 to 2 are suitable. Examples of olefins that may be copolymerized with e.g., maleic anhydride, include 1-decene, 1-dodecene, 1-tetradecene, 1-hexadecene, and 1-octadecene.

The acid or anhydride group of the comb polymer may be esterified by any suitable technique and although preferred it is not essential that the maleic anhydride or fumaric acid be at least 50% esterified. Examples of alcohols which may be used include n-decan-1-ol, n-dodecan-1-ol, n-tetradecan-1-ol, n-hexadecan-1-ol, and noctadecan-1-ol. The alcohols may also include up to one methyl branch per chain, for example, 1-methylpentadecan 1-ol or 2-methyltridecan-1-ol. The alcohol may be a mixture of normal and single methyl branched alcohols.

It is preferred to use pure alcohols rather than the commercially available alcohol mixtures but if mixtures are used the $R^{12}$ refers to the average number of carbon atoms in the alkyl group; if alcohols that contain a branch at the 1 or 2 positions are used $R^{12}$ refers to the straight chain backbone segment of the alcohol.

These comb polymers may especially be fumarate or itaconate polymers and copolymers such for example as those described in EP-A-153176, EP-A-153177 and EP-A-225688, and WO 91/16407.

Particularly preferred fumarate comb polymers are copolymers of alkyl fumarates and vinyl acetate, in which the alkyl groups have from 12 to 20 carbon atoms more especially polymers in which the alkyl groups have 14 carbon atoms or in which the alkyl groups are a mixture of $C_{14}/C_{16}$ alkyl groups, made, for example, by solution copolymerizing an equimolar mixture of fumaric acid and vinyl acetate and reacting the resulting copolymer with the alcohol or mixture of alcohols, which are preferably straight chain alcohols. When the mixture is used it is advantageously a 1:1 by weight mixture of normal $C_{14}$ and $C_{16}$ alcohols. Furthermore, mixtures of the $C_{14}$ ester with the mixed $C_{14}/C_{16}$ ester may advantageously be used. In such mixtures, the ratio of $C_{14}$ to $C_{14}/C_{16}$ is advantageously in the range of from 1:1 to 4:1, preferably 2:1 to 7:2, and most preferably about 3:1, by weight. The particularly preferred comb polymers are those having a number average molecular weight, as measured by vapour phase osmometry, of 1,000 to 100,000, more especially 1,000 to 30,000.

Other suitable comb polymers are the polymers and copolymers of α-olefins and esterified copolymers of styrene and maleic anhydride, and esterified copolymers of styrene and fumaric acid; mixtures of two or more comb polymers may be used in accordance with the invention and, as indicated above, such use may be advantageous. Other examples of comb polymers are hydrocarbon polymers, e.g., copolymers of ethylene and at least one α-olefin, the a-olefin preferably having at most 20 carbon atoms, examples being n-decene-1 and n-dodecene-1. Preferably, the number average molecular weight of such a copolymer is at least 30,000 measured by GPC. The hydrocarbon copolymers may be prepared by methods known in the art, for example using a Ziegler type catalyst.

(C) Polar Nitrogen Compounds

Such compounds are oil-soluble polar nitrogen compounds carrying one or more, preferably two or more, substituents of the formula $>NR^{13}$, where $R^{13}$ represents a hydrocarbyl group containing 8 to 40 atoms, which substituent or one or more of which substituents may be in the form of a cation derived therefrom. The oil soluble polar nitrogen compound is generally one capable of acting as a wax crystal growth inhibitor in fuels. it comprises for example one or more of the following compounds:

An amine salt and/or amide formed by reacting at least one molar proportion of a hydrocarbyl-substituted amine with a molar proportion of a hydrocarbyl acid having from 1 to 4 carboxylic acid groups or its anhydride, the substituent(s) of formula $>NR^{13}$ being of the formula $-NR^{13}R^{14}$ where $R^{13}$ is defined as above and $R^{14}$ represents hydrogen or $R^3$, provided that $R^{13}$, and $R^{14}$ may be the same or different, said substituents constituting part of the amine salt and/or amide groups of the compound.

Ester/amides may be used, containing 30 to 300, preferably 50 to 150, total carbon atoms. These nitrogen compounds are described in U.S. Pat. No. 4,211,534. Suitable amines are predominantly $C_{12}$ to $C_{40}$ primary, secondary, tertiary or quaternary amines or mixtures thereof but shorter chain amines may be used provided the resulting nitrogen compound is oil soluble, normally containing about 30 to 300 total carbon atoms. The nitrogen compound preferably contains at least one straight chain $C_8$ to $C_{40}$, preferably $C_{14}$ to $C_{24}$, alkyl segment.

Suitable amines include primary, secondary, tertiary or quaternary, but are preferably secondary. Tertiary and quaternary amines only form amine salts. Examples of amines include tetradecylamine, cocoamine, and hydrogenated tallow amine. Examples of secondary amines include dioctacedyl amine and methylbehenyl amine. Amine mixtures are also suitable such as those derived from natural materials. A preferred amine is a secondary hydrogenated tallow amine, the alkyl groups of which are derived from hydrogenated tallow fat composed of approximately 4% $C_{14}$, 31% $C_{16}$, and 59% $C_{18}$.

Examples of suitable carboxylic acids and their anhydrides for preparing the nitrogen compounds include ethylenediamine tetraacetic acid, and carboxylic acids based on cyclic skeletons, e.g., cyclohexane-1,2-dicarboxylic acid, cyclohexene-1,2-dicarboxylic acid, cyclopentane-1,2-dicarboxylic acid and naphthalene dicarboxylic acid, and 1,4-dicarboxylic acids including dialkyl spirobislactones. Generally, these acids have about 5 to 13 carbon atoms in the cyclic moiety. Preferred acids useful in the present invention are benzene dicarboxylic acids e.g., phthalic acid, isophthalic acid, and terephthalic acid. Phthalic acid and its anhydride are particularly preferred. The particularly preferred compound is the amide-amine salt formed by reacting 1 molar portion of phthalic anhydride with 2 molar portions of dihydrogenated tallow amine. Another preferred compound is the diamide formed by dehydrating this amide-amine salt.

Other examples are long chain alkyl or alkylene substituted dicarboxylic acid derivatives such as amine salts of monoamides of substituted succinic acids, examples of which are known in the art and described in U.S. Pat. No. 4,147,520, for example. Suitable amines may be those described above.

Other examples are condensates, for example, those described in EP-A-327427.

(D) A Compound Containing a Cyclic Ring System Carrying at Least Two Substituents of the General Formula Below on the Ring System

where A is a linear or branched chain aliphatic hydrocarbylene group optionally interrupted by one or more hetero atoms, and $R^{15}$ and $R^{16}$ are the same or different and each is independently a hydrocarbyl group containing 9 to 40 atoms optionally interrupted by one or more hetero atoms, the substituents being the same or different and the compound optionally being in the form of a salt thereof. Advantageously, A has from 1 to 20 carbon atoms and is preferably a methylene or polymethylene group. Such compounds are described in WO 93/04148.

(E) A Hydrocarbon Polymer

Examples of suitable hydrocarbon polymers are those of the general formula

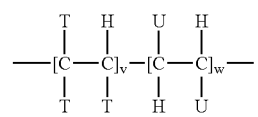

wherein
T=H or $R^{21}$ wherein
$R^{21}=C_1$ to $C_{40}$ hydrocarbyl, and
U=H, T, or aryl and v and w represent mole fractions, v being within the range of from 1.0 to 0.0, w being in the range of from 0.0 to 1.0.

Examples of hydrocarbon polymers are disclosed in WO 91/11488.

Preferred copolymers are ethylene a-olefin copolymers, having a number average molecular weight of at least 30,000. Preferably the α-olefin has at most 28 carbon atoms. Examples of such olefins are propylene, 1-butene, isobutene, n-octene-1, isooctene-1, n-decene-1, and n-dodecene-1. The copolymer may also comprise small amounts, e.g., up to 10% by weight, of other copolymerizable monomers, for example olefins other than α-olefins, and non-conjugated dienes. The preferred copolymer is an ethylene-propylene copolymer.

The number average molecular weight of the ethylene α-olefin copolymer is, as indicated above, preferably at least 30,000, as measured by gel permeation chromatography (GPC) relative to polystyrene standards, advantageously at least 60,000 and preferably at least 80,000. Functionally no upper limit arises but difficulties of mixing result from increased viscosity at molecular weights above about 150, 000, and preferred molecular weight ranges are from 60,000 and 80,000 to 120,000.

Advantageously, the copolymer has a molar ethylene content between 50 and 85 percent. More advantageously, the ethylene content is within the range of from 57 to 80%, and preferably it is in the range from 58 to 73%; more preferably from 62 to 71%, and most preferably 65 to 70%.

Preferred ethylene-α-olefin copolymers are ethylenepropylene copolymers with a molar ethylene content of from 62 to 71% and a number average molecular weight in the range 60,000 to 120,000; especially preferred copolymers are ethylene-propylene copolymers with an ethylene content of from 62 to 71% and a molecular weight from 80,000 to 100,000.

The copolymers may be prepared by any of the methods known in the art, for example using a Ziegler type catalyst. The polymers should be substantially amorphous, since highly crystalline polymers are relatively insoluble in fuel oil at low temperatures.

Other suitable hydrocarbon polymers include a low molecular weight ethylene-α-olefin copolymer, advantageously with a number average molecular weight of at most 7500, advantageously from 1,000 to 6,000, and preferably from 2,000 to 5,000, as measured by vapour phase osmometry. Appropriate α-olefins are as given above, or styrene, with propylene again being preferred. Advantageously the ethylene content is from 60 to 77 molar percent, although for ethylene-propylene copolymers up to 86 molar percent by weight ethylene may be employed with advantage.

(F) A Polyoxyalkylene Compound

Examples are polyoxyalkylene esters, ethers, ester/ethers and mixtures thereof, particularly those containing at least one, preferably at least two, $C_{10}$ to $C_{30}$ linear alkyl groups and a polyoxyalkylene glycol group of molecular weight up to 5,000, preferably 200 to 5,000, the alkyl group in said polyoxyalkylene glycol containing from 1 to 4 carbon atoms. These materials form the subject of EP-A-0061895. Other such additives are described in U.S. Pat. No. 4,491, 455.

The preferred esters, ethers or ester/ethers are those of the general formula $R^{31}$—O(D)-O—$R^{32}$ where $R^{31}$ and $R^{32}$ may be the same or different and represent
(a) n-alkyl—
(b) n-alkyl-CO—
(c) n-alkyl-O—$CO(CH_2)_x$— or 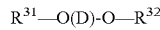
(d) n-alkyl-O—$CO(CH_2)_x$—CO— x being, for example, 1 to 30, the alkyl group being linear and containing from 10 to 30 carbon atoms, and D representing the polyalkylene segment of the glycol in which the alkylene group has 1 to 4 carbon atoms, such as a polyoxymethylene, polyoxyethylene or polyoxytrimethylene moiety which is substantially linear; some degree of branching with lower alkyl side chains (such as in polyoxypropylene glycol) may be present but it is preferred that the glycol is substantially linear. D may also contain nitrogen.

Examples of suitable glycols are substantially linear polyethylene glycols (PEG) and polypropylene glycols (PPG) having a molecular weight of from 100 to 5,000, preferably from 200 to 2,000. Esters are preferred and fatty acids containing from 10-30 carbon atoms are useful for reacting with the glycols to form the ester additives, it being preferred to use a $C_{18}$-$C_{24}$ fatty acid, especially behenic acid. The esters may also be prepared by esterifying polyethoxylated fatty acids or polyethoxylated alcohols.

Polyoxyalkylene diesters, diethers, ether/esters and mixtures thereof are suitable as additives, diesters being preferred for use in narrow boiling distillates, when minor amounts of monoethers and monoesters (which are often formed in the manufacturing process) may also be present. It is preferred that a major amount of the dialkyl compound be present. In particular, stearic or behenic diesters of polyethylene glycol, polypropylene glycol or polyethylene/polypropylene glycol mixtures are preferred.

Other examples of polyoxyalkylene compounds are those described in Japanese Patent Publication Nos. 2-51477 and 3-34790, and the esterified alkoxylated amines described in EP-A-117108 and EP-A-326356.

EXAMPLES

Iron salts of neodecanoic acid were tested for their stability in fuel oil over extended periods of time. The iron in the treated fuel was monitored at two levels: 10 ppm and 40 ppm. One salt was 90 mole % ferric and 10 mole % ferrous (based on total iron present) and the other was 50 mole % ferric and 50 mole % ferrous (based on total iron present). Two samples of the 90% ferric salt and one sample of the 50% ferric salt were tested by being stored at room temperature and observed periodically for evidence of deposit formation. Both samples of the 90% ferric salt remained stable and showed no evidence of deposits after 75 days. The 50% ferric sample showed deposits after 40 days.

The invention claimed is:

1. A fuel additive iron salt composition effective in improving the operation of diesel engine particulate traps when added to a diesel fuel so as to provide 1-25 ppm iron in the fuel which comprises an oil soluble or oil dispersible neutral or overbased iron salt of an acidic organic compound, 60-90 mole % of the total iron in the composition being in the ferric form, the balance being the ferrous form, wherein when the additive is added to fuel oil and stored at room temperature for a period less than or equal to 40 days, the fuel oil does not show deposits.

2. The composition of claim 1 wherein the salt is selected from the group consisting of sulfonates, phenates, sulfurized phenates, salicylates, naphthenates and carboxylates.

3. The composition of claim 1 wherein the salt is overbased and the excess iron is in the form of an oxide, carbonate or hydroxide.

4. The composition of claim 1 wherein the salt is a neocarboxylate or naphthenate.

5. A fuel additive iron salt composition effective in improving the operation of diesel engine particulate traps when added to a diesel fuel so as to provide 1-25 ppm iron in the fuel which comprises an oil soluble or oil dispersible overbased iron salt of an acidic organic compound, 50-90 mole % of the total iron in the composition being in the ferric form, the balance being the ferrous form, wherein the excess iron is present in an amount of 5-85 wt. % of a stoichiometric excess over the amount required to neutralize the anionic portion of the salt and wherein when the additive is added to fuel oil and stored at room temperature for a period less than or equal to 40 days, the fuel oil does not show deposits.

6. The composition of claim 1 wherein the salt is a carboxylate.

7. The composition of claim 1 wherein the salt is a neocarboxylate or naphthenate.

8. A diesel fuel composition containing an effective amount of a composition of comprising 1-25 ppm iron from an oil soluble or oil dispersible neutral or overbased iron salt of an acidic organic compound, 60-90 mole % of the total iron in the composition being in the ferric form, the balance being the ferrous form, wherein when the composition is added to fuel oil and stored at room temperature for a period less than or equal to 40 days, the fuel oil does not show deposits.

9. The composition of claim 8 wherein the salt is selected from the group consisting of sulfonates, phenates, sulfurized phenates, salicylates, naphthenates and carboxylates.

10. The composition of claim 8 wherein the iron is 60 mol % or more ferric.

11. The composition of claim 8 wherein the salt is overbased and the excess iron is in the form of an oxide, carbonate or hydroxide.

12. The composition of claim 8 wherein the excess iron is in the form of an oxide.

13. The composition of claim 10 wherein the salt is a neocarboxylate.

14. The composition of claim 11 wherein the excess iron is present in an amount of 20-50 wt. %.

15. The composition of claim 8 wherein the salt is a carboxylate.

16. The composition of claim 8 where the salt is a neocarboxylate or naphthenate.

* * * * *